United States Patent
Malecha et al.

(10) Patent No.: US 9,500,618 B2
(45) Date of Patent: *Nov. 22, 2016

(54) ANALYTE MEASUREMENT METHOD AND SYSTEM

(71) Applicant: LifeScan Scotland Limited, Inverness (GB)

(72) Inventors: Michael Malecha, Muir of Ord (GB); Adam Craggs, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/606,317

(22) Filed: Jan. 27, 2015

(65) Prior Publication Data

US 2015/0136615 A1    May 21, 2015

Related U.S. Application Data

(62) Division of application No. 13/637,220, filed as application No. PCT/GB2011/000783 on Mar. 30, 2011, now Pat. No. 8,962,270.

(60) Provisional application No. 61/319,470, filed on Mar. 31, 2010.

(51) Int. Cl.
    *G01N 27/327*    (2006.01)
    *G06F 19/10*    (2011.01)

(52) U.S. Cl.
    CPC ...... *G01N 27/3274* (2013.01); *G01N 27/3273* (2013.01); *G06F 19/10* (2013.01)

(58) Field of Classification Search
    CPC .................................. G01N 27/327–27/3274
    See application file for complete search history.

(56) References Cited

U.S. PATENT DOCUMENTS

| 6,241,862 B1 | 6/2001 | McAleer et al. |
| 6,576,117 B1 | 6/2003 | Iketaki et al. |

(Continued)

FOREIGN PATENT DOCUMENTS

| CN | 1991355 A | 7/2007 |
| CN | 1975403 B | 12/2011 |

(Continued)

OTHER PUBLICATIONS

Notice of Reasons for Rejection issued in related Japanese Patent Application No. 2013-501929, dated Nov. 18, 2014, 5 pages.

(Continued)

*Primary Examiner* — J. Christopher Ball

(57) ABSTRACT

Described and illustrated herein are systems and exemplary methods of operating an analyte measurement system having a meter and a test strip. In one embodiment, the method may be achieved by applying a first test voltage between a reference electrode and a second working electrode and applying a second test voltage between the reference electrode and a first working electrode; measuring a first test current, a second test current, a third test current and a fourth test current at the second working electrode after a blood sample containing an analyte is applied to the test strip; measuring a fifth test current at the first working electrode; estimating a hematocrit-corrected analyte concentration from the first, second, third, fourth and fifth test currents; and annunciating the hematocrit-corrected analyte concentration.

7 Claims, 12 Drawing Sheets

(56) References Cited

U.S. PATENT DOCUMENTS

| | | | |
|---|---|---|---|
| 7,132,041 | B2 | 11/2006 | Deng et al. |
| 7,749,371 | B2 | 7/2010 | Guo et al. |
| 8,088,272 | B2 | 1/2012 | Deng |
| 8,425,757 | B2 | 4/2013 | Wu et al. |
| 8,962,270 | B2 * | 2/2015 | Malecha ............ G01N 27/3273 435/14 |
| 2002/0139692 | A1 | 10/2002 | Tokunaga et al. |
| 2007/0084734 | A1 | 4/2007 | Roberts et al. |
| 2009/0184004 | A1 | 7/2009 | Chatelier et al. |
| 2009/0236237 | A1 | 9/2009 | Shinno et al. |
| 2009/0280551 | A1 | 11/2009 | Cardosi et al. |
| 2009/0301899 | A1 | 12/2009 | Hodges et al. |
| 2011/0073494 | A1 * | 3/2011 | McColl ............... G01N 27/3271 205/777.5 |

FOREIGN PATENT DOCUMENTS

| | | |
|---|---|---|
| CN | 1558224 B | 8/2013 |
| DE | 102006043718 A1 | 3/2008 |
| EP | 2042865 A2 | 4/2009 |
| JP | 2001153839 A | 6/2001 |
| JP | 2004264217 A | 9/2004 |
| JP | 2009503452 A | 1/2009 |
| JP | 2009168815 A | 7/2009 |
| JP | 2009294213 A | 12/2009 |
| JP | 2010506162 A | 2/2010 |
| TW | 200914820 | 4/2009 |
| WO | 9960391 A1 | 11/1999 |
| WO | 2008004565 A1 | 1/2008 |
| WO | 2008040998 A2 | 4/2008 |
| WO | WO 2008/040998 A2 * | 4/2008 |

OTHER PUBLICATIONS

Second Office Action issued in related Chinese Patent Application No. 201180026678.1, issued Jul. 30, 2014, 12 pages.

Chinese Search Report for Application No. 201180026678.1, mail date: Jan. 6, 2014.

European Search Report for Application No. 12195075.2-1554/2565636, mail date: Mar. 6, 2013.

European Search Report for Application No. 12195112.3-1554/2565637, mail date: Mar. 6, 2013.

European Search Report for Application No. 12195155.2-1554/2565638, mail date: Mar. 6, 2013.

International Search Report for International Application No. PCT/GB2011/000483, mail date: Oct. 17, 2012.

Patent Examination Report issued in related Australian Patent Application No. 2011234255, dated Nov. 26, 2013, 2 pages.

Third Office Action issued in related Chinese Patent Application No. 201180026678.1, issued Jan. 29, 2015, 10 pages.

Search Report issued in related Chinese Patent Application No. 201180026678.1, dated Feb. 10, 2015, 2 pages (English translation only).

Official Action of substantive examination issued in related Russian Patent Application No. 2012146333, Feb. 13, 2015, 9 pages.

International Preliminary Report on Patentability issued in related International Patent Application No. PCT/GB2011/000483, mailed Oct. 11, 2012, 12 pages.

* cited by examiner

ANALYTE MEASUREMENT METHOD AND SYSTEM

CROSS-REFERENCE

This DIVISIONAL application claims the benefits of priority under 35 USC §§120 and 121 from prior filed U.S. application Ser. No. 13/637,220 filed on Mar. 30, 2011, allowed, which prior filed application (Ser. No. 13/637,220) claims the benefits under 35 USC§§119, 120, 365, and 371 of prior filed U.S. Provisional Application Ser. No. 61/319,470 filed on Mar. 31, 2010, and International Patent Application No. PCT/GB2011/000483 filed on Mar. 30, 2011, which applications are incorporated by reference in their entirety into this application.

BACKGROUND

Electrochemical sensors have been used to detect or measure the presence of substances in fluid samples. Electrochemical sensors include a reagent mixture containing at least an electron transfer agent (also referred to as an "electron mediator") and an analyte specific bio-catalytic protein (e.g. a particular enzyme), and one or more electrodes. Such sensors rely on electron transfer between the electron mediator and the electrode surfaces and function by measuring electrochemical redox reactions. When used in an electrochemical biosensor system or device, the electron transfer reactions are monitored via an electrical signal that correlates to the concentration of the analyte being measured in the fluid sample.

The use of such electrochemical sensors to detect analytes in bodily fluids, such as blood or blood derived products, tears, urine, and saliva, has become important, and in some cases, vital to maintain the health of certain individuals. In the health care field, people such as diabetics, for example, must monitor a particular constituent within their bodily fluids. A number of systems are capable of testing a body fluid, such as, blood, urine, or saliva, to conveniently monitor the level of a particular fluid constituent, such as, cholesterol, proteins, and glucose. Patients suffering from diabetes, a disorder of the pancreas where insufficient insulin production prevents the proper digestion of sugar, have a need to carefully monitor their blood glucose levels on a daily basis. Routine testing and controlling blood glucose for people with diabetes can reduce their risk of serious damage to the eyes, nerves, and kidneys.

Electrochemical biosensors may be adversely affected by the presence of certain blood components that may undesirably affect the measurement and lead to inaccuracies in the detected signal. This inaccuracy may result in an inaccurate glucose reading, leaving the patient unaware of a potentially dangerous blood sugar level, for example. As one example, the blood hematocrit level (i.e. the percentage of the amount of blood that is occupied by red blood cells) can erroneously affect a resulting analyte concentration measurement.

Variations in a volume of red blood cells within blood can cause variations in glucose readings measured with disposable electrochemical test strips. Typically, a negative bias (i.e., lower calculated analyte concentration) is observed at high hematocrit, while a positive bias (i.e., higher calculated analyte concentration) is observed at low hematocrit. At high hematocrit, for example, the red blood cells may impede the reaction of enzymes and electrochemical mediators, reduce the rate of chemistry dissolution since there less plasma volume to solvate the chemical reactants, and slow diffusion of the mediator. These factors can result in a lower than expected glucose reading as less current is produced during the electrochemical process. Conversely, at low hematocrit, fewer red blood cells may affect the electrochemical reaction than expected, and a higher measured current can result. In addition, the blood sample resistance is also hematocrit dependent, which can affect voltage and/or current measurements.

Several strategies have been used to reduce or avoid hematocrit based variations on blood glucose. For example, test strips have been designed to incorporate meshes to remove red blood cells from the samples, or have included various compounds or formulations designed to increase the viscosity of red blood cell and attenuate the affect of low hematocrit on concentration determinations. Other test strips have included lysis agents and systems configured to determine hemoglobin concentration in an attempt to correct hematocrit. Further, biosensors have been configured to measure hematocrit by measuring optical variations after irradiating the blood sample with light, or measuring hematocrit based on a function of sample chamber fill time. These sensors have certain disadvantages.

SUMMARY OF THE DISCLOSURE

Applicants have recognized a need for a system and method that can be used to determine an accurate glucose concentration that avoids the disadvantages in the field.

In view of the foregoing and in accordance with one aspect, there is provided a method of operating an analyte measurement system having a meter and a test strip. The test strip may include a reference electrode, a first working electrode and a second working electrode in which the first electrodes are coated with a reagent layer. The meter may include an electronic circuit for applying a test voltage between the reference electrode and the first working electrode and for applying a second test voltage between the reference electrode and the second working electrode. The meter also may include a signal processor for measuring a plurality of test currents and for calculating a glucose concentration from the test currents. The method may be achieved by applying a first test voltage between the reference electrode and the second working electrode and applying a second test voltage between the reference electrode and the first working electrode; measuring a first test current, a second test current, a third test current and a fourth test current at the second working electrode after a blood sample containing an analyte is applied to the test strip; measuring a fifth test current at the first working electrode; ascertaining the glucose concentration from the first, second, third, fourth and fifth test currents; and annunciating the glucose concentration.

In the exemplary method, the glucose concentration may be a value obtained with the following:

$$G = \frac{\left[\left(\frac{I_1}{I_2}\right)^{\left(a-b\frac{I_3}{I_4}\right)} x I_5\right] - \text{intercept}}{\text{slope}}$$

where:
G is the hematocrit-corrected glucose concentration;
$I_1$ is the first test current;
$I_2$ is the second test current;
$I_3$ is the third test current;

$I_4$ is the second test current;
$I_5$ is the third test current;
a and b are tuning parameters that are empirically derived;
intercept is an intercept value determined from a linear regression of a plot of $$\left[\left(\frac{I_1}{I_2}\right)^{\left(a-b\frac{I_3}{I_4}\right)} xI_5\right]$$

versus a reference glucose concentration; and
slope is a slope value determined from a linear regression of a plot of $$\left[\left(\frac{I_1}{I_2}\right)^{\left(a-b\frac{I_3}{I_4}\right)} xI_5\right]$$

versus the reference glucose concentration.

In an embodiment in which first and second test voltages are applied to the test strip as soon as a test fluid is detected, the first tuning parameter a may be from about 9.5 to about 10.5 and the second tuning parameter b may be from about 10.5 and 11.5. In another embodiment in which first and second test voltages are applied to the test strip after the test fluid is allowed to react for a period of time with the reagent layer, first tuning parameter a may be from about 31.5 to about 32.5 and second tuning parameter b may be from about 53.5 and 54.5.

In yet a further embodiment, a method for determining a hematocrit-corrected test current measurable with a system having a test strip and a meter is provided. The method can be achieved by applying a first test voltage between a reference electrode and a second working electrode coated with a reagent layer and applying a second test voltage between the reference electrode and a first working electrode; measuring a first test current, a second test current, a third test current and a fourth test current at the second working electrode after a blood sample containing an analyte is applied to the test strip; measuring a fifth test current at the first working electrode and ascertaining a hematocrit-corrected test current via a ratio of the first test current to the second test current raised to a power term and multiplying the ratio by the fifth test current, in which the power term is a function of a first tuning parameter and a second tuning parameter.

In yet a further embodiment, an analyte measurement system to measure at least glucose concentration in physiological fluid of a user is provided. The system includes a test strip and a meter. The test strip includes a substrate having a reference electrode, a first working electrode and a second working electrode, all of which are coated with a reagent layer. The electrodes are connected to corresponding contact pads. The analyte meter has a test circuit in connection with a test strip port that receives the contact pads of the test strip so that the meter is configured to apply first and second test voltages to respective second and first working electrode after deposition of physiological fluid on the electrodes and to determine a hematocrit-corrected glucose concentration from measured first, second, third, fourth and fifth test currents at first, second, third, fourth and fifth discrete intervals after application of the test voltages by the meter.

These and other embodiments, features and advantages of the invention will become apparent to those skilled in the art when taken with reference to the following more detailed description of the exemplary embodiments in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (in which like numerals represent like elements), of which.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1A:
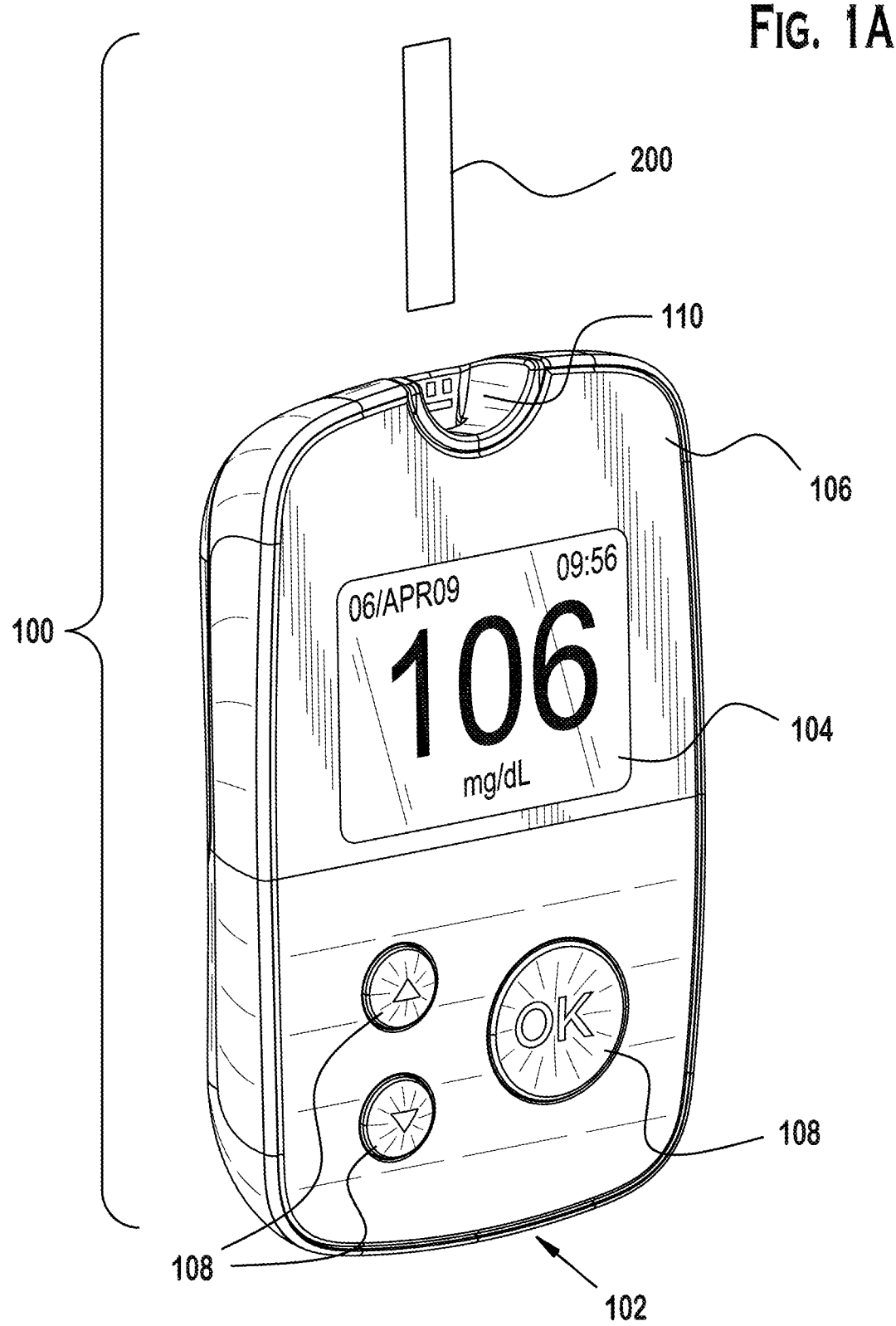
FIG. 1A illustrates an exemplary embodiment of a top view of a system for measuring an analyte concentration.

FIG. 1A illustrates a system 100 for measuring an analyte concentration in which system 100 may include a meter 102 and a test strip 120. Meter 102 may include a display 104, a housing 106, a plurality of user interface buttons 108, and a strip port 110. Meter 102 further may include electronic circuitry within housing 106 as further described in relation to FIG. 1B. A proximal portion of test strip 120 may be inserted into strip port 110. Display 104 may annunciate an analyte concentration, e.g., glucose concentration, and may be used to show a user interface for prompting a user on how to perform a test. As used here, the term "annunciate" and variations on the root term indicate that an announcement may be provided via text, audio, visual or a combination of all modes of communication to a user, a caretaker of the user, or a healthcare provider. The plurality of user interface buttons 108 allow a user to operate meter 102 by navigating through the user interface software. Display 104 may optionally include a backlight.

Figure 1B:
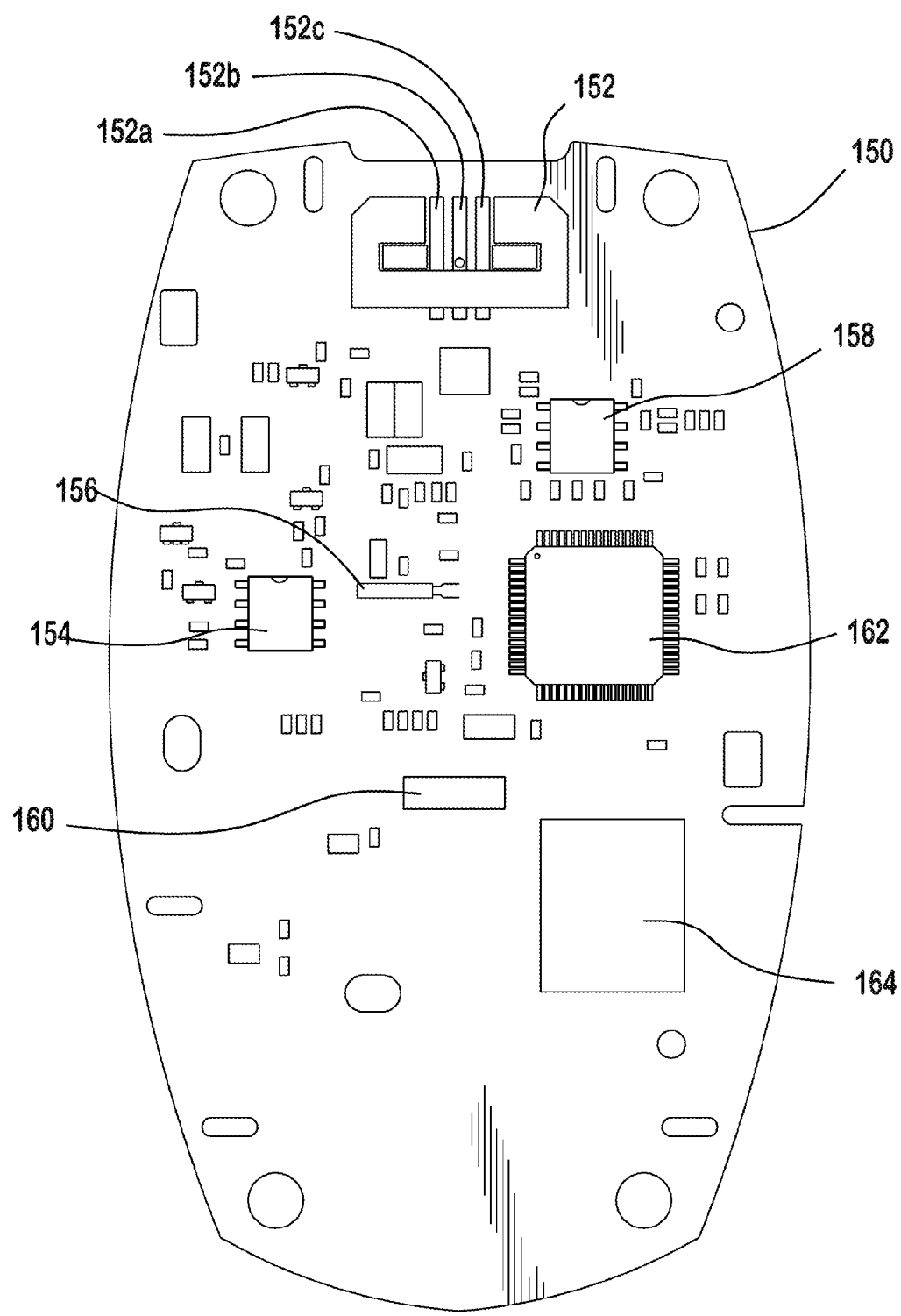
FIG. 1B illustrates an exemplary circuit board of the electrical components disposed in the analyte measurement device of FIG. 1A.

Disposed inside housing 106 includes, as shown in FIG. 1B, a circuit board 150 with a microcontroller 162 coupled to a memory 154, clock 156, operational amplifier 158, and display connector 160. The op-amp 158 and microcontroller 162 are operatively connected to a strip port connector 152 with contacts 152a, 152b, and 152b for mechanical contact with corresponding conductive tracks on the test strip 120. To facilitate communication with other data management devices, a wireless transceiver module 164 is provided to allow for bi-directional communication of data stored in the memory 154 of the unit 100. On the other side of circuit board 150 a power source in the form of a battery (not shown) is provided. A data port may also be provided. It should be noted that the meter unit 100 is preferably sized and configured to be handheld and the transceiver 164 can be for use with either or both of a short-range wireless network (e.g., BlueTooth or Wi-Fi and the like) or a longer range wireless network (e.g., GSM, CDMA, 3G and the like).

Microcontroller 162 can be electrically connected to strip port 152, operational amplifier circuit 158, first wireless module 164, display 104, non-volatile memory 154, clock 156, data port, and user interface buttons 108. Data entered via the buttons, transceiver or glucose measurement circuit can include values representative of analyte concentration, or in the context of the analyte concentration values coupled with information, which are related to the everyday lifestyle of an individual. Information, which is related to the everyday lifestyle, can include food intake, medication use, occurrence of health check-ups, and general health condition and exercise levels of an individual coupled to or "tagged" with the analyte concentration value of the user at specific time of the day or week.

Operational amplifier circuit 158 can be two or more operational amplifiers configured to provide a portion of the potentiostat function and the current measurement function. The potentiostat function can refer to the application of a test voltage between at least two electrodes of a test strip. The current function can refer to the measurement of a test current resulting from the applied test voltage to the test strip 120. The current measurement may be performed with a current-to-voltage converter. Microcontroller 162 can be in the form of a mixed signal microprocessor (MSP) such as, for example, the Texas Instrument MSP430F2419. The TI-MSP430F2419 can be configured to also perform a portion of the potentiostat function and the current measurement function. In addition, the MSP430F2419 can also include volatile and non-volatile memory. In another embodiment, many of the electronic components can be integrated with the microcontroller in the form of an application specific integrated circuit (ASIC).

Strip port 152 can be configured to form an electrical connection to the test strip. Display connector 160 can be configured to attach to display 104. Display 104 can be in the form of a liquid crystal display for reporting measured glucose levels, and for facilitating entry of lifestyle related information and for manipulation of graphical data, pictorial results and motion video. Display 104 may also include a backlight. Data port can accept a suitable connector attached to a connecting lead, thereby allowing meter unit 100 to be linked to an external device such as a personal computer. Data port can be any port that allows for transmission of data such as, for example, a serial, USB, or a parallel port. Clock 156 can be configured for measuring time and be in the form of an oscillating crystal.

Figure 2:
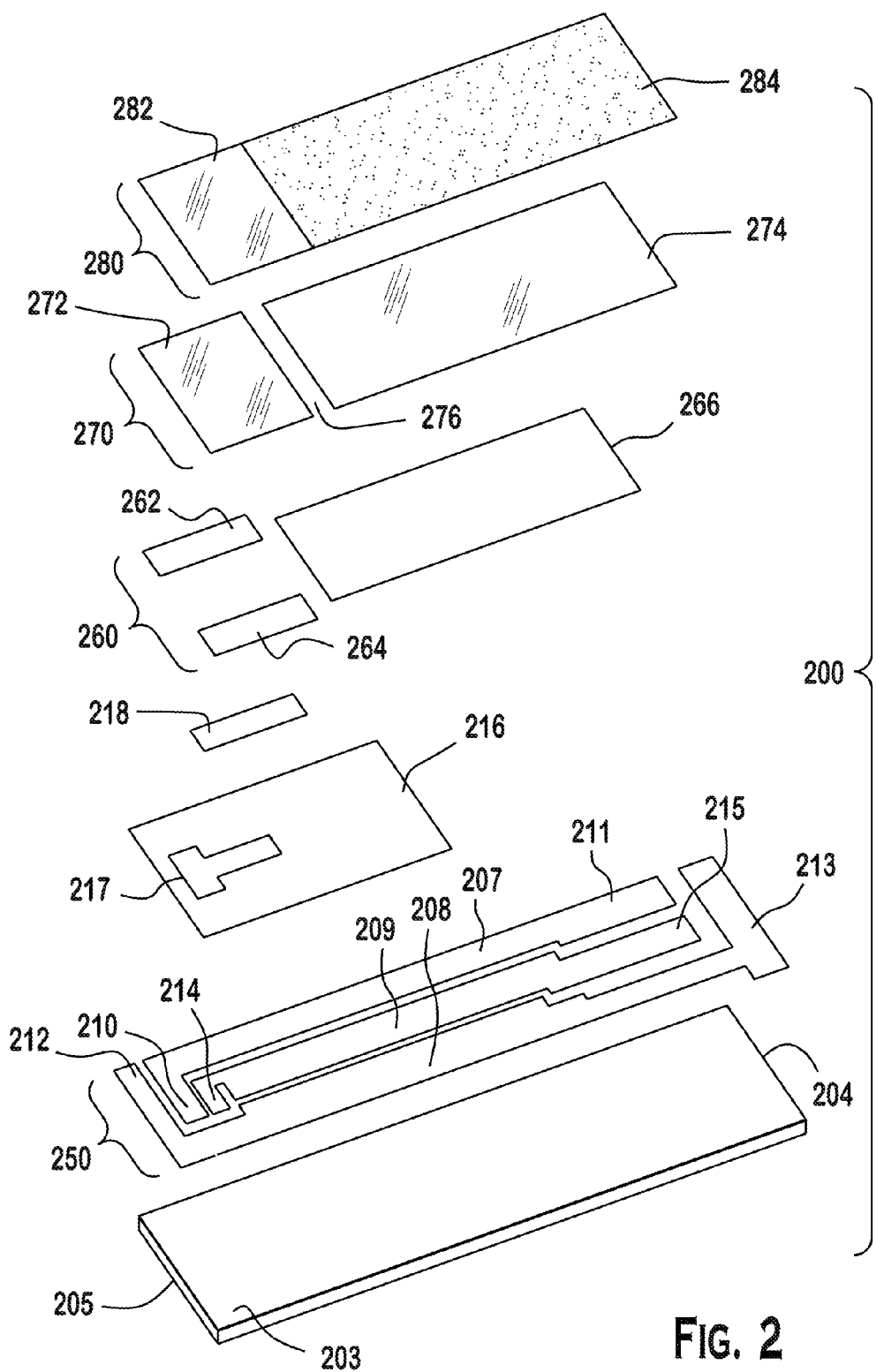
FIG. 2 illustrates an exemplary embodiment of a perspective exploded view of a test strip.
Figure 3:
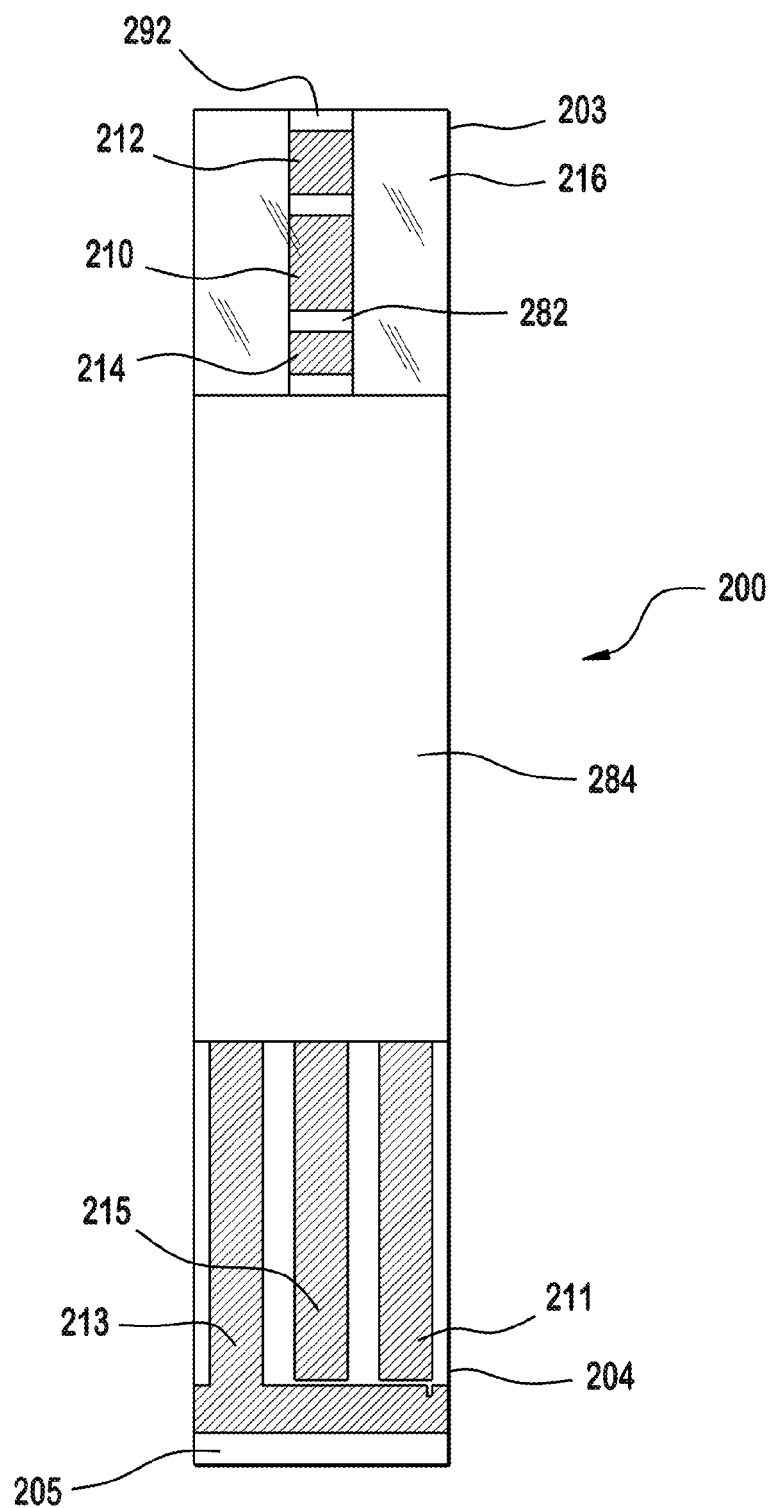
FIG. 3 illustrates an exemplary embodiment of a top view of the test strip shown in FIG. 2.

FIGS. 2 and 3 are exemplary exploded perspective and top assembled views, respectively, of test strip 120, which may include seven layers disposed on a substrate 205. The seven layers disposed on substrate 205 may be a conductive layer 250, an insulation layer 216, a reagent layer 218, an adhesive layer 260, a hydrophilic layer 270, and a top layer 280. Test strip 120 may be manufactured in a series of steps where the conductive layer 250, insulation layer 216, reagent layer 218, and adhesive layer 260 are sequentially deposited on substrate 205 using, for example, a screen-printing process. Hydrophilic layer 270 and top layer 280 may be disposed from a roll stock and laminated onto substrate 205 as either an integrated laminate or as separate layers. Test strip 120 has a distal portion 203 and a proximal portion 204, as shown in FIG. 2.

Test strip 120 may include a sample-receiving chamber 292 through which a blood sample may be drawn. Sample-receiving chamber 292 may include an inlet at a proximal end of test strip 120. An outlet or air vent is included in hydrophilic layer 270, as will be described below. A blood sample may be applied to the inlet to fill a sample-receiving chamber 292 so that an analyte concentration may be measured. The side edges of a cut-out portion of adhesive layer 260 located adjacent to reagent layer 218 defines a wall of sample-receiving chamber 292, as illustrated in FIG. 2. A bottom portion or "floor" of sample-receiving chamber 292 may include a portion of substrate 205, conductive layer 250, and insulation layer 216. A top portion or "roof" of sample-receiving chamber 292 may include distal hydrophilic portion 282.

For test strip 120, as illustrated in FIG. 2, substrate 205 may be used as a foundation for helping support subsequently applied layers. Substrate 205 may be in the form of a polyester sheet such as a polyethylene tetraphthalate (PET) material. Substrate 205 may be in a roll format, nominally 350 microns thick by 370 millimeters wide and approximately 60 meters in length.

A conductive layer 250 is required for forming electrodes that may be used for the electrochemical measurement of glucose. Conductive layer 250 may be made from a carbon ink that is screen-printed onto substrate 205. In a screen-printing process, carbon ink is loaded onto a screen and then transferred through the screen using a squeegee. The printed carbon ink may be dried using hot air at about 140° C. The carbon ink may include VAGH resin, carbon black, graphite, and one or more solvents for the resin, carbon and graphite mixture. More particularly, the carbon ink may incorporate a suitable ratio of carbon black:VAGH resin in the carbon ink.

For test strip 120, as illustrated in FIG. 2, conductive layer 250 may include a reference electrode 210, a first working electrode 212, a second working electrode 214, a reference contact pad 211, a first contact pad 213, a second contact pad 215, a reference electrode track 207, a first working electrode track 208 and a second working electrode track 209. In the embodiment shown in FIG. 2, reference electrode 210 is located in between first working electrode 212 and second electrode 214 such that cross-talk between first and second working electrodes 212 and 214 is minimized.

Conductive layer 250 may be formed from a carbon ink. Reference contact pad 211, first contact pad 213 and second contact pad 215 may be configured to electrically connect to a test meter. Reference electrode track 207 provides an electrically continuous pathway from reference electrode 210 to reference contact pad 211. Similarly, first working electrode track 208 provides an electrically continuous pathway from first working electrode 12 to first contact pad 213. Similarly, second working electrode track 209 provides an electrically continuous pathway from second working electrode 214 to second contact pad 215.

Insulation layer 216 may include an aperture 217 that exposes a portion of reference electrode 210, first working electrode 212, and second working electrode 214, which may be wetted by a liquid sample. The area of first working electrode 212, second working electrode 214, and reference electrode 210 may be defined as the area exposed to the liquid sample. In addition to defining an electrode area, insulation layer 216 prevents a liquid sample from touching the electrode tracks 207, 208, and 209. It is believed that the functional area of a working electrode should be accurately defined because the magnitude of the test current is directly proportional to the effective area of the electrode. As an example, insulation layer 216 may be Ercon E6110-116 Jet Black Insulayer™ ink that may be purchased from Ercon, Inc. The test strip at this point may be treated with plasma. The plasma is created by high voltage AC at atmospheric temperatures and pressures. The resulting plasma, consisting of ionised, highly energetic particles is swept downstream in an air current to impact the substrate. Plasma treatment is used to modify the surface of the screen-printed carbon based electrodes. This surface modification is believed to increase the electrochemical activity of the carbon surface and increases the surface energy of the printed layers allowing for better adhesion between them and subsequently printed layers. Plasma treatment is also believed to improve the electrochemistry of the carbon surface making the reaction with the mediator more ideal as part of the electrochemical reaction during a measurement cycle.

Reagent layer 218 is disposed on a portion of conductive layer 250 and insulation layer 216, as illustrated in FIG. 2. In an embodiment, two overlapping reagent layers may be printed over a portion of conductive layer 250 and insulation layer 216.

Reagent layer 218 may include chemicals such as an enzyme and a mediator which selectivity reacts with an analyte of interest and a buffer for maintaining a desired pH. For example, if glucose is to be determined in a blood sample, reagent layer 218 may include an enzyme and a mediator, along with other components necessary for functional operation. Enzymatic reagent layer 18 may include, for example, glucose oxidase, tri-sodium citrate, citric acid, polyvinyl alcohol, hydroxyl ethyl cellulose, potassium ferricyanide, antifoam, cabosil, PVPVA, and water.

Exemplary enzymes suitable for use in the reagent layer include glucose oxidase, glucose dehydrogenase with a pyrroloquinoline quinone (PQQ) co-factor and glucose dehydrogenase with a flavin adenine dinucleotide (FAD) co-factor. An exemplary mediator suitable for use in the reagent layer includes ferricyanide, which in this case is in the oxidized form. The reagent layer may be configured to physically transform glucose into an enzymatic by-product and in the process generate an amount of reduced mediator (e.g., ferrocyanide) that is proportional to the glucose concentration value. Further details regarding reagent layers, and electrochemical-based analytical test strips in general, are in U.S. Pat. No. 6,241,862, the contents of which are hereby fully incorporated by reference.

In one embodiment, the area of reagent layer 218 is sufficiently large to cover the entire area of reference electrode 210, first working electrode 212 and second working electrode 214. Reagent layer 218 includes a width and a length that is sufficiently large to at least account for the largest electrode area that may be used in test strip 120. The width of reagent layer 218 may be about 2 millimeters, which is more than double a width of rectangular aperture 217.

Adhesive layer 260 includes a first adhesive pad 262, a second adhesive pad 264 and a third adhesive pad 266 and may be disposed on test strip 120 after the deposition of reagent layer 218. Portions of adhesive layer 260 may be aligned to be immediately adjacent to, touch, or partially overlap with reagent layer 218. Adhesive layer 260 may include a water based acrylic copolymer pressure sensitive adhesive that is commercially available. Adhesive layer 260 is disposed on a portion of insulation layer 216, conductive layer 250, and substrate 205. Adhesive layer 260 binds hydrophilic layer 270 to test strip 120.

Hydrophilic layer 270 may include a distal hydrophilic portion 272 and proximal hydrophilic portion 274, as illustrated in FIG. 2. A gap 276 is included between distal hydrophilic portion 272 and proximal hydrophilic portion 274. Gap 276 serves as a side vent for air as blood fills sample-receiving chamber 292 (shown in FIG. 3). Hydrophilic layer 270 may be a polyester material having one hydrophilic surface such as an anti-fog coating, which is commercially available from 3M.

The final layer to be added to test strip 120 is top layer 280, as illustrated in FIG. 2. Top layer 280 may include a clear portion 282 and opaque portion 284. Top layer 280 is disposed on and adhered to hydrophilic layer 270. Top layer 280 may be a polyester that has an adhesive coating on one side. It should be noted that the clear portion 282 substantially overlaps distal hydrophilic portion 272, which allows a user to visually confirm that sample-receiving chamber 292 may be sufficiently filled. Opaque portion 238 helps the user observe a high degree of contrast between a colored fluid such as, for example, blood within sample-receiving chamber 292 and opaque portion 284.

Figure 4:
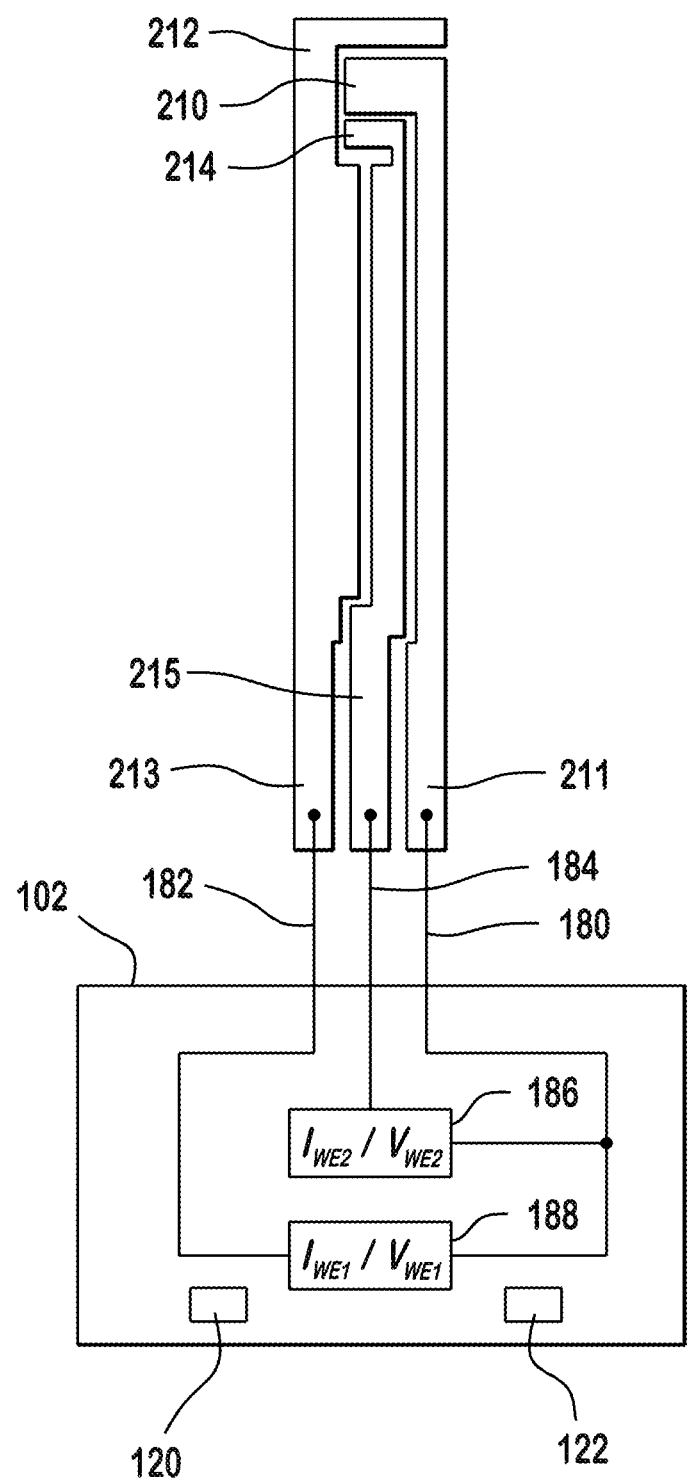
FIG. 4 illustrates an exemplary embodiment of a schematic of the functional components of the meter shown in FIG. 1A forming an electrical connection with the test strip of FIGS. 2 and 3.

FIG. 4 shows a simplified schematic of meter 102 interfacing with test strip 120. Meter 102 may include a reference connector 180, a first connector 182 and a second connector 184, which respectively form an electrical connection to reference contact 211, first contact 213 and second contact 215. The three aforementioned connectors are part of strip port 110. When performing a test, a first test voltage source 186 (from the circuit of FIG. 1B) may apply a test voltage $V_{WE2}$ between second working electrode 214 and reference electrode 210. As a result of test voltage $V_{WE2}$, meter 102 may then measure a test current $I_{WE2}$ at second working electrode. In a similar manner, a second test voltage source 188 (from the circuit of FIG. 1B) applies a test voltage $V_{WE1}$ between first working electrode 212 and reference electrode 210. As a result of test voltage $V_{WE1}$, meter 102 may then measure a test current $I_{WE1}$. In an embodiment, test voltage $V_{WE2}$ and second test voltage $V_{WE1}$ may be about equal.

Figure 5:
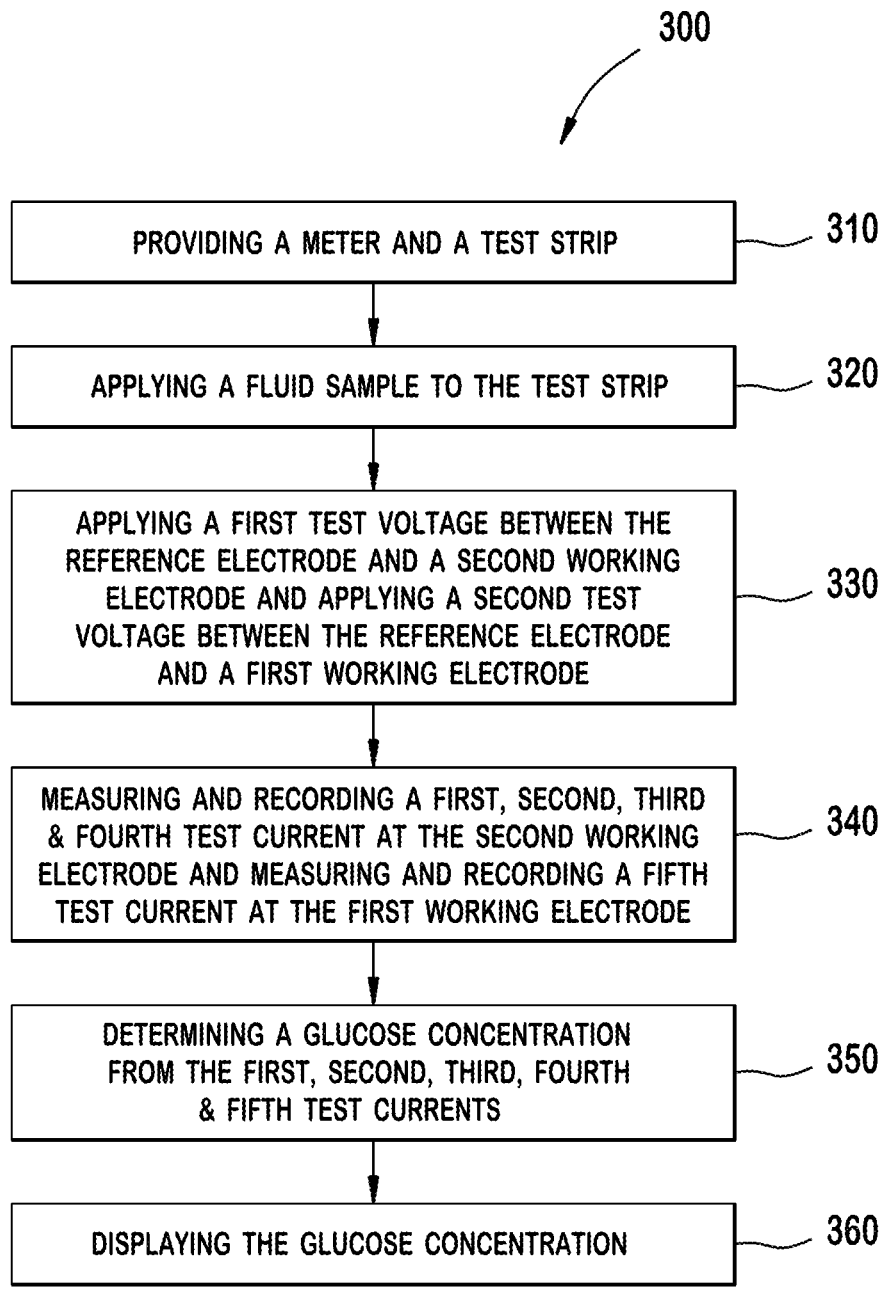
FIG. 5 illustrates an exemplary embodiment of a flow chart of a method of estimating a hematocrit-corrected glucose concentration using the system shown in FIG. 1A.

Referring to FIG. 5, a method 300 for determining a hematocrit-corrected analyte concentration (e.g., glucose) that uses the aforementioned meter 102 and test strip 120 embodiments will now be described.

In exemplary step 310, meter 102 and test strip 120 are provided. Meter 102 may include electronic circuitry that can be used to apply a first and second test voltage to the test strip and to measure current flowing through the second working electrode 214 and the first working electrode 212, respectively. Meter 102 also may include a signal processor with a set of instructions for the method of determining an analyte concentration in a fluid sample as disclosed herein. In one embodiment, the analyte is blood glucose.

Figure 6A:
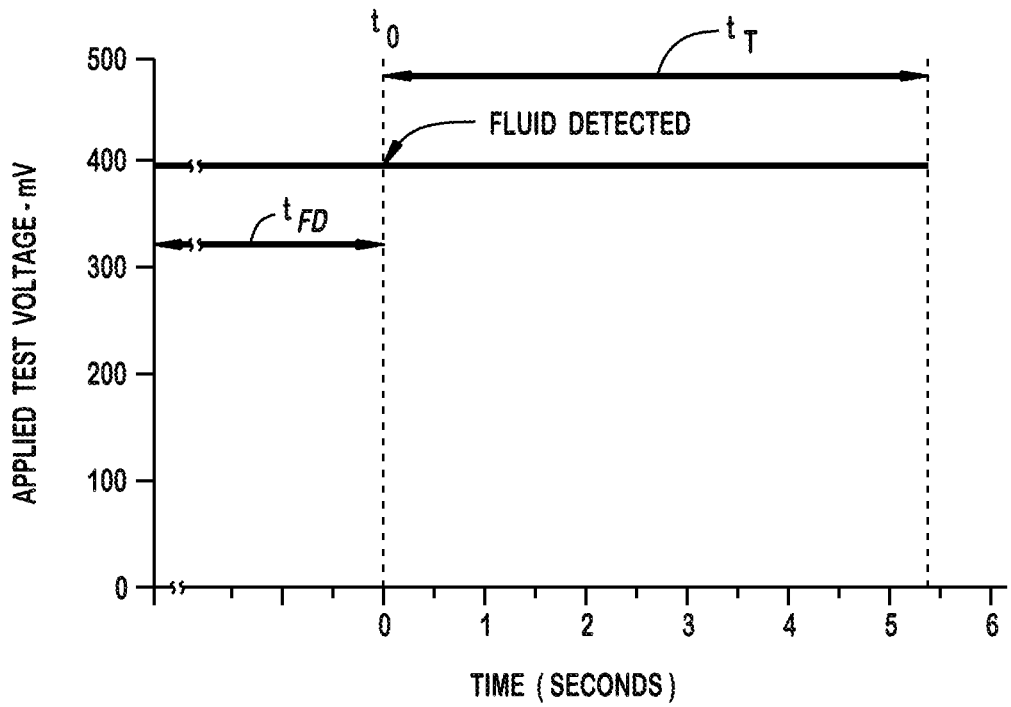
FIG. 6A illustrates an exemplary embodiment of a chart showing test voltages applied by the meter to the test strip.

FIG. 6A is an exemplary chart of a test voltage applied to test strip 120. Before a fluid sample is applied to test strip 120, test meter 102 is in a fluid detection mode in which a first test voltage of about 400 millivolts is applied between second working electrode 214 and reference electrode 210. A second test voltage of about 400 millivolts is preferably applied simultaneously between first working electrode 212 and reference electrode 210. Alternatively, the second test voltage may also be applied contemporaneously such that a time interval of the application of the first test voltage overlaps with a time interval in the application of the second test voltage. The test meter may be in a fluid detection mode during fluid detection time interval $t_{FD}$ prior to the detection of physiological fluid at time $t_0$. In the fluid detection mode, test meter 120 determines when a fluid is applied to test strip 120 in exemplary step 320 such that the fluid wets second working electrode 214 and reference electrode 210. Once test meter 120 recognizes that the physiological fluid has been applied because of, for example, a sufficient increase in the measured test current at second working electrode 214, test meter 120 assigns a zero second marker at time $t_0$ and starts the test time interval $t_T$. Upon the completion of the test time interval $t_T$, the test voltage is removed. For simplicity, FIG. 6A only shows the first test voltage applied to test strip 120.

Figure 6B:
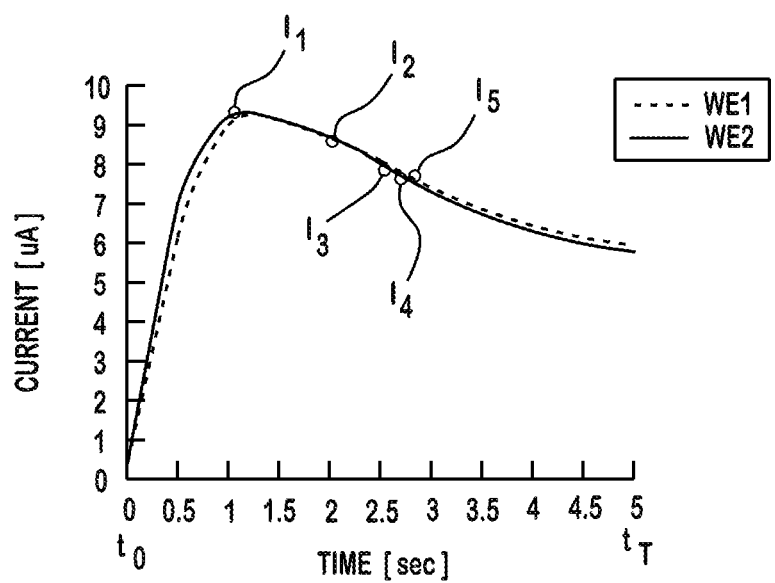
FIG. 6B illustrates an exemplary embodiment of a chart showing test currents generated when the test voltages of FIG. 6A are applied to the test strip.

FIG. 6B is an exemplary chart of current transients (i.e., the measured electrical current response in nanoamperes as a function of time) that are measured when the test voltages of FIG. 6A are applied to test strip 120. Test currents $I_i$ obtained from current transients are generally indicative of the analyte concentration in the sample as will be described in exemplary step 370 below. Referring to FIGS. 5 and 6A, in exemplary step 330, the first test voltage is applied between second working electrode 214 and reference electrode 210 and a second test voltage is applied between first working electrode 212 and reference electrode 210 at time $t_0$. In exemplary step 340, a first test current $I_1$, a second test current $I_2$, a third test current $I_3$ and a fourth test current $I_4$ are measured at times $t_2$, $t_3$, $t_4$ and $t_5$, respectively, at second working electrode 214. These currents $I_i$ where i=1, 2, 3, 4 ... n are stored or recorded in the memory unit of the meter for analysis. In exemplary step 340, a fifth test current $I_5$ is also measured at time $t_6$ at first working electrode 212. The first and second test voltages applied to test strip 120 are generally from about +100 millivolts to about +600 millivolts. In one embodiment in which the electrodes include carbon ink and the mediator is ferricyanide, the test voltage is about +400 millivolts. Other mediator and electrode material combinations will require different test voltages. The duration of the test voltages is generally from about 2 to about 4 seconds after a reaction period and is typically about 3 seconds after a reaction period. Typically, time $t_i$ is measured relative to time $t_0$. In practice, each test current $I_i$ is the average of a set of measurements obtained over a short interval, for example, five measurements obtained at 0.01 second intervals starting at $t_{i+1}$, where i ranges from 1 to at least 6.

Referring to FIG. 5 in exemplary step 350, a hematocrit-corrected glucose concentration may be determined with the following:

$$G = \frac{\left[\left(\frac{I_1}{I_2}\right)^{\left(a-b\frac{I_3}{I_4}\right)} xI_5\right] - \text{intercept}}{\text{slope}} \quad (1)$$

where:
G is the hematocrit-corrected glucose concentration;
$I_1$ is the first test current;
$I_2$ is the second test current;
$I_3$ is the third test current;
$I_4$ is the second test current;
$I_5$ is the third test current;
a and b are tuning parameters that are empirically derived;
intercept is an intercept value determined from a linear regression of a plot of $$\left[\left(\frac{I_1}{I_2}\right)^{\left(a-b\frac{I_3}{I_4}\right)} xI_5\right]$$

versus a reference glucose concentration; and
slope is a slope value determined from a linear regression of a plot of $$\left[\left(\frac{I_1}{I_2}\right)^{\left(a-b\frac{I_3}{I_4}\right)} xI_5\right]$$

versus the reference glucose concentration.

In an embodiment, first test current $I_1$ may be measured at about 0.98 seconds to about 1.00 seconds after time $t_0$, second test current $I_2$ may be measured at about 1.98 seconds to about 2.00 seconds after time $t_0$, third test current $I_3$ may be measured at about 2.43 seconds to about 2.45 seconds after time $t_0$, fourth test current may be measured at about 2.61 seconds to about 2.63 seconds after time $t_0$ and fifth test current may be measured at about 2.70 seconds to about 2.72 seconds after time $t_0$.

In an embodiment, a is a first tuning parameter from about 9.9 to about 10.2 and b is a second tuning parameter from about 10.8 to about 11.2.

In exemplary step 360, the hematocrit-corrected glucose concentration may then be annunciated on meter 102.

Figure 7:
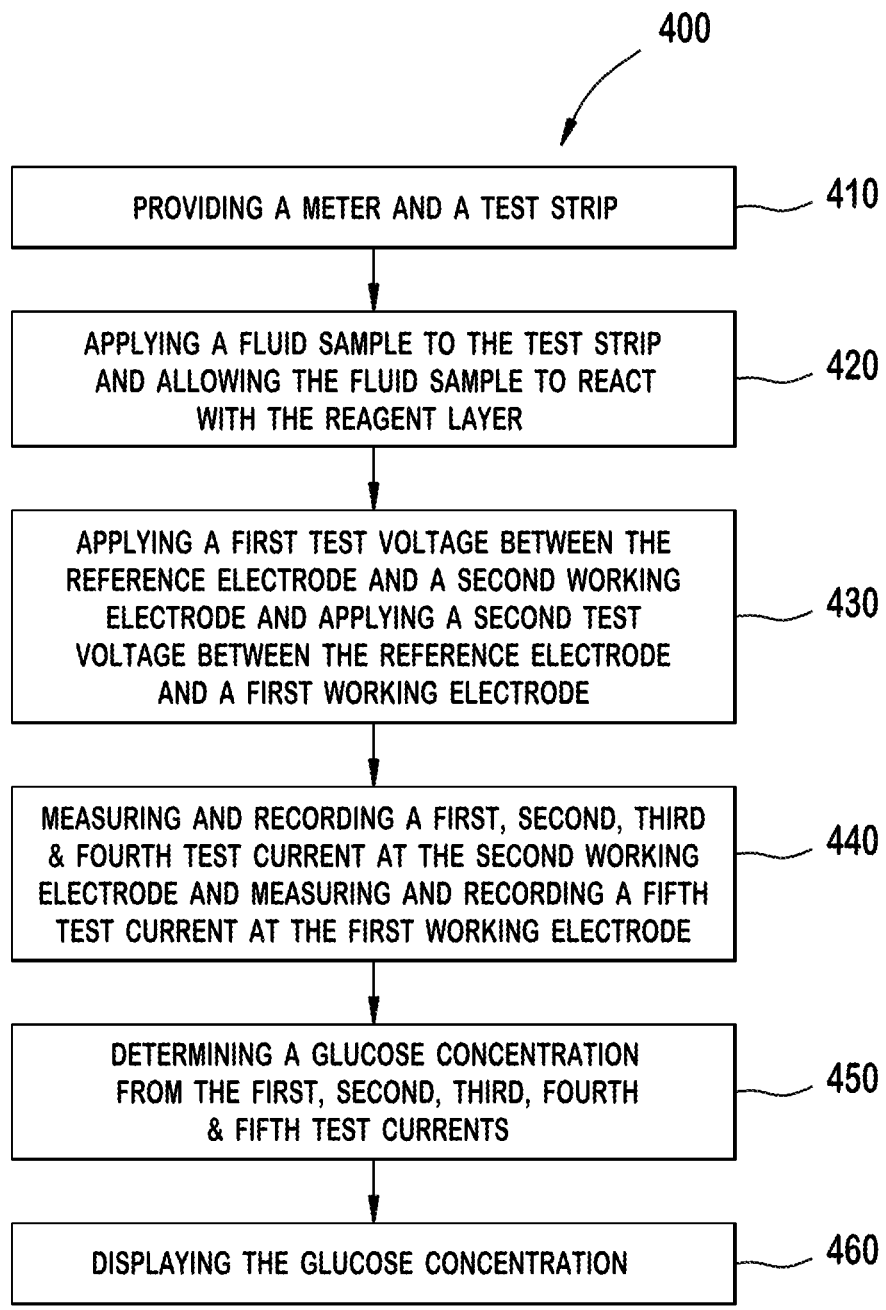
FIG. 7 illustrates another exemplary embodiment of a flow chart of a method of estimating a hematocrit-corrected glucose concentration using the system shown in FIG. 1A.

Referring to FIG. 7, another method 400 for determining a hematocrit-corrected analyte concentration (e.g., glucose) that uses the aforementioned meter 102 and test strip 120 embodiments will now be described.

In exemplary step 410, meter 102 and test strip 120 are provided. Meter 102 may include electronic circuitry that can be used to apply a first and second test voltage to the test strip and to measure current flowing through the second working electrode 214 and the first working electrode 212, respectively. Meter 102 also may include a signal processor with a set of instructions for the method of determining an analyte concentration in a fluid sample as disclosed herein. In one embodiment, the analyte is blood glucose.

Figure 8A:
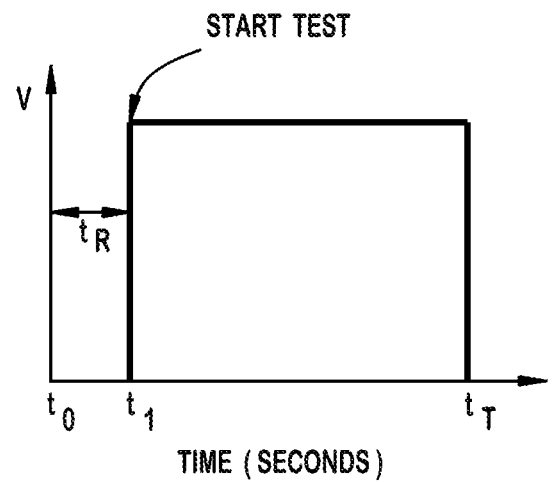
FIG. 8A illustrates an exemplary embodiment of a chart showing test voltages applied by the meter to the test strip.

FIG. 8A is an exemplary chart of a test voltage applied to test strip 120. Before a fluid sample is applied to test strip 120, test meter 102 is in a fluid detection mode in which a first test voltage of about 400 millivolts is applied between second working electrode 214 and reference electrode 210. A second test voltage of about 400 millivolts is also applied between first working electrode 212 and reference electrode 210. In exemplary step 420, the fluid sample is applied to test strip 100 at $t_0$ and is allowed to react with reagent layer 218 for a reaction period $t_R$. The presence of sample in the reaction zone of test strip 120 is determined by measuring the current flowing through second working electrode 214. The beginning of reaction period $t_R$ is determined to begin when the current flowing through second working electrode 214 reaches a desired value, typically about 150 nanoamperes (not shown), at which point a test voltage of about zero millivolts is applied between second working electrode 214 and reference electrode 210 and between first working electrode 212 and reference electrode 210. Reaction period $t_R$ is typically from about 2 to about 4 seconds after initiation of the measuring and is more typically about 3 seconds after initiation of the measuring, i.e., after $t_1$. In exemplary step 430, after reaction period $t_R$, first and second test voltages are applied to test strip 120 at $t_1$ for a total test time $t_T$. For simplicity, FIG. 8A only shows the first test voltage applied to test strip 120.

Figure 8B:
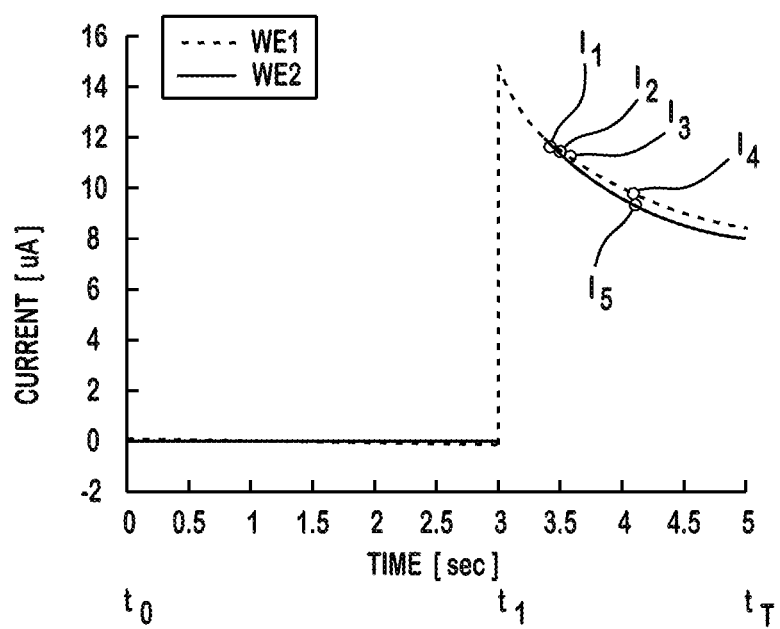
FIG. 8B illustrates an exemplary embodiment of a chart showing test currents generated when the test voltages of FIG. 8A are applied to the test strip.

FIG. 8B is an exemplary chart of current transients that are measured when the test voltages of FIG. 8A are applied to test strip 120. Test currents $I_i$ obtained from current transients are generally indicative of the analyte concentration in the sample as will be described in exemplary step 470 below. Referring to FIGS. 7 and 8A, in exemplary step 440, after the first and second test voltages are applied to test strip 120 at time $t_1$, a first test current $I_1$, a second test current $I_2$, a third test current $I_3$ and a fourth test current $I_4$ are measured at times $t_2$, $t_3$, $t_4$ and $t_5$, respectively, at second working electrode 214. In exemplary step 440, a fifth test current $I_5$ is also measured at time $t_6$ at first working electrode 212. The first and second test voltages applied to test strip 120 are generally from about +100 millivolts to about +600 millivolts. In one embodiment in which the electrodes are carbon ink and the mediator is ferricyanide, the test voltages are about +400 millivolts. Other mediator and electrode material combinations may require different test voltages. The duration of test voltages is generally from about 4 and 6 seconds after a reaction period and is typically about 5 seconds after a reaction period. Typically, time $t_i$ is measured relative to time $t_1$. In practice, each test current $I_i$ is the average of a set of measurements obtained over a short interval, for example, five measurements obtained at 0.01 second intervals starting at $t_{i+1}$, where I ranges from 1 to 6.

Referring to FIG. 7, in exemplary step 470, a hematocrit-corrected glucose concentration may be determined with Equation 1 as described previously.

In an embodiment, first test current $I_1$ may be measured at about 3.37 seconds to about 3.39 seconds after reaction period $t_R$, second test current $I_2$ may be measured at about 3.46 seconds to about 3.48 seconds after reaction period $t_R$, third test current $I_3$ may be measured at about 3.54 seconds to about 3.56 seconds after reaction period $t_R$, fourth test current may be measured at about 4.05 seconds to about 4.07 seconds after reaction period $t_R$ and fifth test current may be measured at about 4.08 seconds to about 4.10 seconds after reaction period $t_R$.

In an embodiment, a is a first tuning parameter from about 31 to about 33 and b is a second tuning parameter from about 53 to about 55.

In exemplary step 480, the hematocrit-corrected glucose concentration may then be annunciated on meter 102.

Example 1

Determination of Hematocrit-Corrected Glucose Concentration in which No Reaction Period is Allowed for a Fluid Sample to React with the Reagent Layer A batch of test strips was tested with 2118 whole blood samples having three different glucose concentrations (i.e., 50 mg/dL, 240 mg/dL and 450 mg/dL) and hematocrit levels ranging from 30 to 55%. Test currents were measured at the second working electrode at 0.99, 1.99, 2.44 and 2.62 seconds and at the first working electrode at 2.71 seconds. The hematocrit-corrected glucose concentration was determined for each data point as described previously with method 300 (i.e., no reaction period prior to application of the test voltages). Empirically derived tuning parameters a and b having values of 10.05 and 10.99, respectively, were used in Equation 1 to determine the hematocrit-corrected glucose concentration along with an empirically derived slope of 0.0136 and an intercept of 0.312.

An uncorrected glucose concentration was also determined for over two thousands whole blood samples (specifically about 2122 samples) having three different glucose concentrations (i.e., 50 mg/dL, 240 mg/dL and 450 mg/dL) and hematocrit levels ranging from 30 to 55%. The same batch of test strips was used. A test current at 5 seconds (hereinafter called the "end current") was measured and recorded for each sample. The uncorrected glucose concentration was then determined from a calibration curve table stored in the meter. A calibration curve may be generated from the end current data by graphing end current as a function of known glucose concentration as measured on a reference instrument.

Example 2

Determination of Hematocrit-Corrected Glucose Concentration in which a Fluid Sample is Allowed to React with the Reagent Layer for a Reaction Period The same batch of test strips as used in Example 1 was tested with approximately 2150 whole blood samples having three different glucose concentrations (i.e., 50 mg/dL, 240 mg/dL and 450 mg/dL) and hematocrit levels ranging from about 30% to about 55%. Test currents were measured at the second working electrode at approximately 3.4, 3.5, 3.6 and 4.1 seconds and at the first working electrode at 4.1 seconds. The hematocrit-corrected glucose concentration was determined for each data point as described previously with method 400 (i.e., reaction period prior to application of the test voltages). Empirically derived tuning parameters a and b having values of approximately 32.03 and 53.96, respectively, were used in Equation 1 to determine the hematocrit-corrected glucose concentration along with an empirically derived slope of approximately 0.0103 and an intercept of approximately 0.377.

The bias, which is an estimate of the relative error in the glucose measurement, was next calculated for each glucose concentration determined with the three methods described in Examples 1 and 2 (i.e., endpoint current, method 300 and method 400). The bias for each glucose concentration was determined with equations of the form:

$$Bias_{abs} = G_{calculated} - G_{reference} \text{ for } G_{reference} \text{ less than 75 mg/dL glucose and}$$

$$Bias_{\%} = \frac{G_{calculated} - G_{reference}}{G_{reference}} \text{ for } G_{reference}$$

greater than or equal to 75 mg/dL glucose where $Bias_{abs}$ is absolute bias, $Bias_{\%}$ is percent bias, $G_{calculated}$ is the glucose concentration determined by one of three methods described in Examples 1 and 2 and $G_{reference}$ is the reference glucose concentration.

Figure 9:
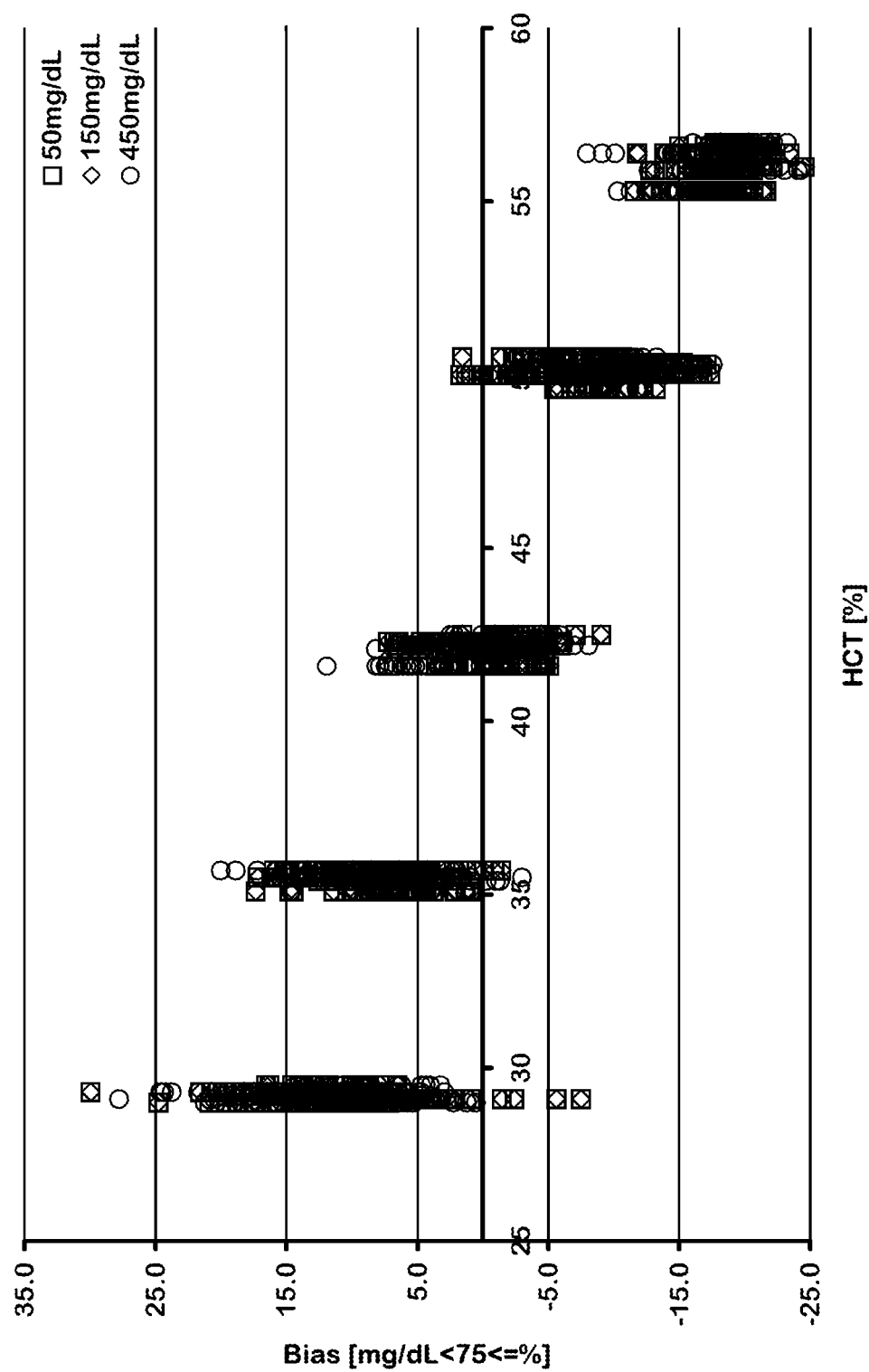
FIG. 9 illustrates a bias plot of test data obtained with an end current algorithm.
Figure 10:
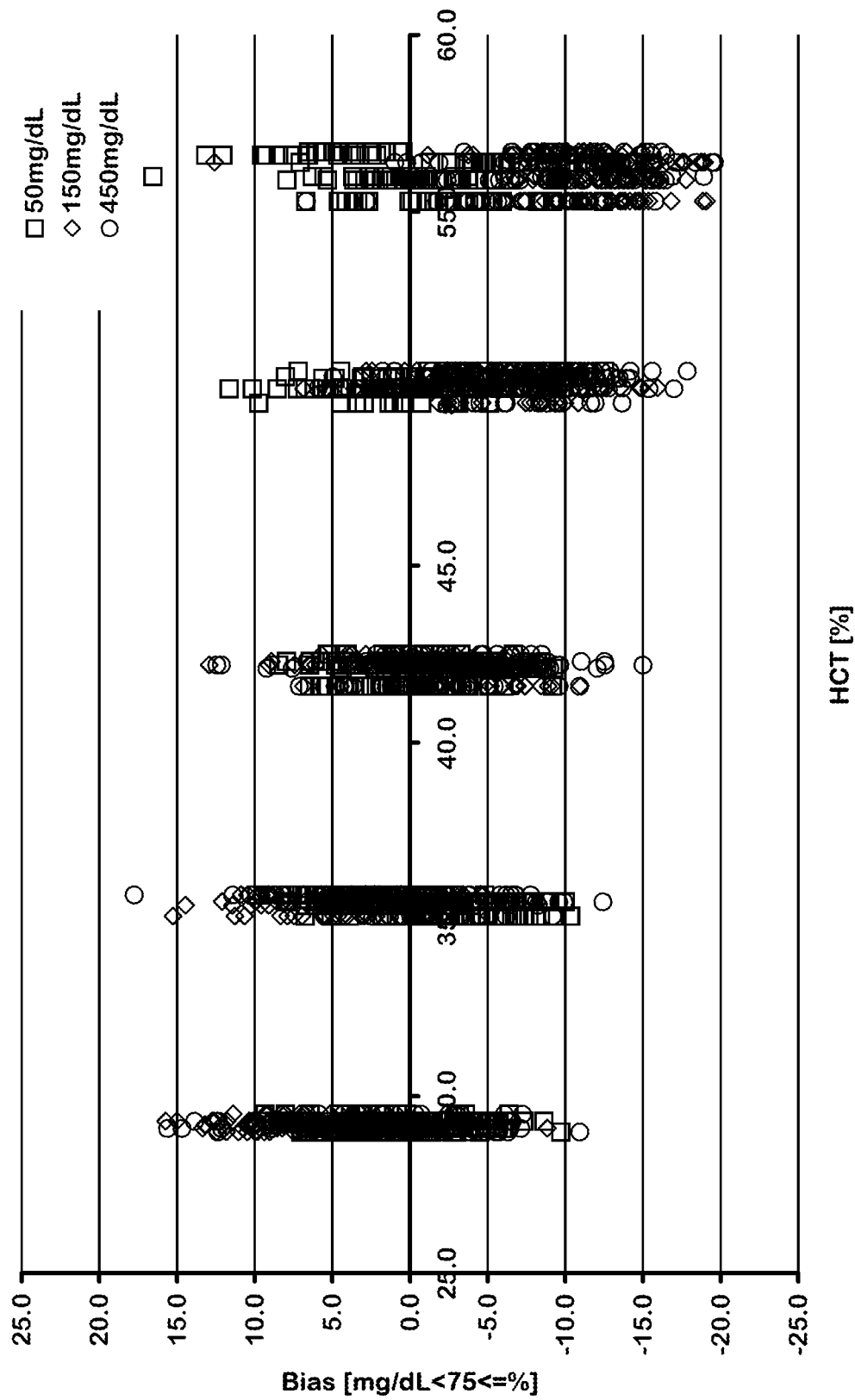
FIG. 10 illustrates a bias plot of test data obtained with a method of the current invention in which the test voltage is applied to the test strip as shown in FIG. 6A.
Figure 11:
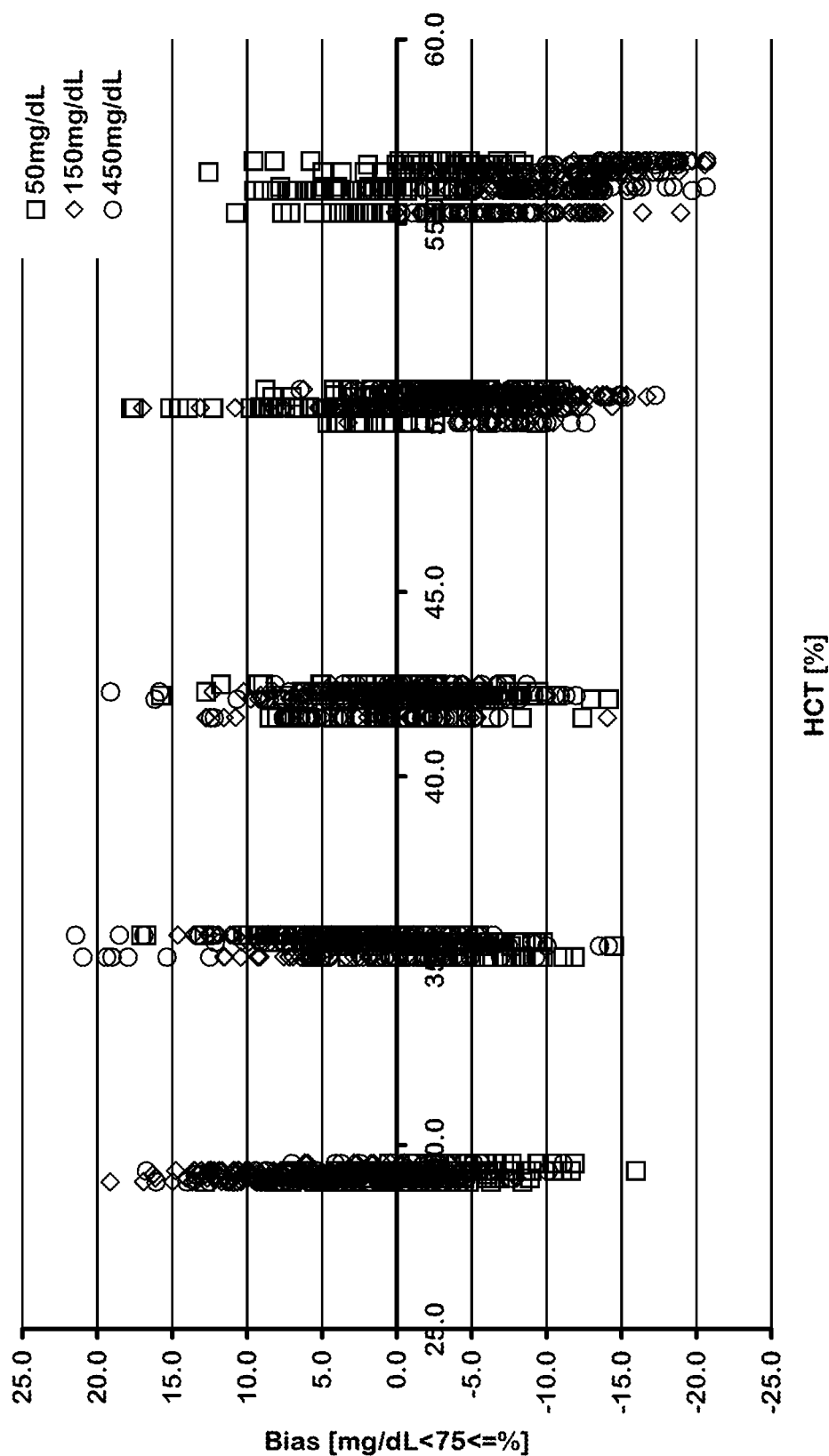
FIG. 11 illustrates a bias plot of test data obtained with a method of the current invention in which the test voltage is applied to the test strip as shown in FIG. 7A.

FIGS. 9, 10 and 11 illustrate bias plots of bias versus percent hematocrit. FIG. 9 illustrates the bias plot of data in which the end current was used to determine the glucose concentration. FIG. 10 illustrates the bias plot of data as determined by method 300 (i.e., no reaction period prior to application of the test voltages). FIG. 11 illustrates the bias plot of data as determined by method 400 (i.e., reaction period prior to application of the test voltages).

The data from FIGS. 9, 10 and 11 may also be presented as a percent falling within different ISO (International Standards Organization) bias criteria, as illustrated in Table 1 below.

TABLE 1

Summary of Bias Results

| ISO Bias Criteria Approx. (%) | Percent within Bias Criteria for Endpoint algorithm | Percent within Bias Criteria for Method 300 | Percent within Bias Criteria for Method 400 |
|---|---|---|---|
| +/−20 | 96.7 | 100 | 99.7 |
| +/−15 | 84.0 | 97.4 | 96.0 |
| +/−10 | 68.4 | 85.7 | 83.3 |

The data in Table 1 indicates an increase in the percent of data falling within each ISO bias criteria when methods 300 and 400 are used to correct the data for the hematocrit effect.

In conclusion, the system and methods described and illustrated herein can be used to determine a hematocrit-corrected glucose concentration. Thus, the glucose result obtained with the exemplary subject system and method is believed to be more accurate.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method for determining a glucose concentration measurable with a system having a test strip and a meter, the method comprising:

applying a first test voltage between a reference electrode and a second working electrode coated with a reagent layer and applying a second test voltage between a reference electrode and a first working electrode coated with a reagent layer;

measuring a first test current, a second test current, a third test current and a fourth test current at the second working electrode after a blood sample containing glucose is applied to the test strip;

measuring a fifth test current at the first working electrode;

determining the glucose concentration from the first, second, third, fourth and fifth test currents with an equation of the form:

$$G = \frac{\left[\left(\frac{I_1}{I_2}\right)^{\left(a-b\frac{I_3}{I_4}\right)} xI_5\right] - \text{intercept}}{\text{slope}}$$

where:
G is the glucose concentration;
$I_1$ is the first test current;
$I_2$ is the second test current;
$I_3$ is the third test current;
$I_4$ is the fourth test current;
$I_5$ is the fifth test current;
a is a first tuning parameter and b is a second tuning parameter.

2. The method of claim 1, in which first tuning parameter is from about 9.9 to about 10.2 and second tuning parameter is from about 10.8 to about 11.2.

3. A method for determining a hematocrit-corrected test current measurable with a system having a test strip and a meter, the method comprising:

applying a first test voltage between a reference electrode and a second working electrode coated with a reagent layer and applying a second test voltage between a reference electrode and a first working electrode coated with a reagent layer;

measuring a first test current, a second test current, a third test current and a fourth test current at the second working electrode after a blood sample containing glucose is applied to the test strip;

measuring a fifth test current at the first working electrode; and determining the hematocrit-corrected test current by determining a ratio of the first test current to the second test current raised to a power term and multiplying the ratio by the fifth test current, where the power term is a function of a first tuning parameter and a second tuning parameter.

4. The method of claim 3, in which first tuning parameter is from about 31 to 33 and second tuning parameter is from about 53 to about 55; the first test current comprises a current measured from about 0.9 to about 1.0 seconds after initiation of the measuring; the second current comprises a current measured from about 1.1 to about 2.0 seconds after initiation of the measuring; the third current comprises a current measured from about 2.4 to about 2.5 seconds after initiation of the measuring; the fourth current comprises a current measured from about four 2.61 to about 2.63 seconds after initiation of the measuring; the fifth current comprises a current measured from about 2.70 to about 2.72 seconds after initiation of the measuring.

5. The method of claim 3, in which no test voltage is applied for a period of time after the deposition of the physiological fluid to provide for a reaction time before application of the test voltage.

6. The method of claim 5, in which the first test current is measured from about 3.37 to about 3.39 seconds after a reaction period of time; the second current is measured from about 3.46 to about 3.48 seconds after a reaction period of time; the third current is measured from about 3.54 to about 3.56 seconds after a reaction period of time; the fourth current is measured from about 4.05 to about 4.07 seconds after a reaction period of time; the fifth current is measured from about 4.08 to about 4.10 seconds after a reaction period of time.

7. The method of claim 6, in which the reference electrode, the first electrode and the second electrodes are disposed on one plane.

\* \* \* \* \*